(12) United States Patent
Conway

(10) Patent No.: US 6,905,485 B2
(45) Date of Patent: Jun. 14, 2005

(54) MEDICAL DEVICE WITH NEEDLE SAFETY SHIELDING

(75) Inventor: Hugh T. Conway, Verona, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 10/369,790

(22) Filed: Feb. 19, 2003

(65) Prior Publication Data

US 2004/0162523 A1 Aug. 19, 2004

(51) Int. Cl.[7] .................................................. A61M 5/32
(52) U.S. Cl. ............................................................. 604/198
(58) Field of Search .............................. 604/162, 164.08, 604/263, 198, 44, 82, 110, 177

(56) References Cited

U.S. PATENT DOCUMENTS

| | | |
|---|---|---|
| 4,943,283 A | 7/1990 | Hogan |
| 4,946,446 A | 8/1990 | Vadher |
| 5,186,712 A | 2/1993 | Kelso et al. |
| 5,192,275 A | 3/1993 | Burns |
| 5,295,975 A | 3/1994 | Lockwood, Jr. |
| 5,403,286 A * | 4/1995 | Lockwood, Jr. ............ 604/110 |
| 5,480,385 A | 1/1996 | Thorne et al. |
| 5,718,239 A | 2/1998 | Newby et al. |
| 5,746,215 A | 5/1998 | Manjarrez |
| 5,893,845 A | 4/1999 | Newby et al. |
| 6,210,371 B1 | 4/2001 | Shaw |
| 6,254,577 B1 | 7/2001 | Huet |
| 6,368,303 B1 | 4/2002 | Caizza |
| 2002/0045843 A1 | 4/2002 | Barker et al. |
| 2002/0099339 A1 | 7/2002 | Niermann |
| 2002/0103464 A1 | 8/2002 | Crawford et al. |

* cited by examiner

Primary Examiner—Kevin C. Sirmons

(57) ABSTRACT

With the present invention, needle safety shielding is provided for medical devices, such as blood collection sets. In a broadest sense, the invention is a medical device which includes a first needle cannula mounted to a first needle hub; a second needle cannula; tubing having a first lumen for establishing fluid communication between the first and second needle cannulas; an actuatable shield movable relatively to the first needle cannula upon actuation from an initial first position where the first needle cannula is at least partially exposed to a second position where a sharp distal end of the first needle cannula is protected or at least partially encapsulated by the shield; and, an actuator for actuating the shield which is engageable at a location spaced from the first needle cannula and the first needle hub.

23 Claims, 5 Drawing Sheets

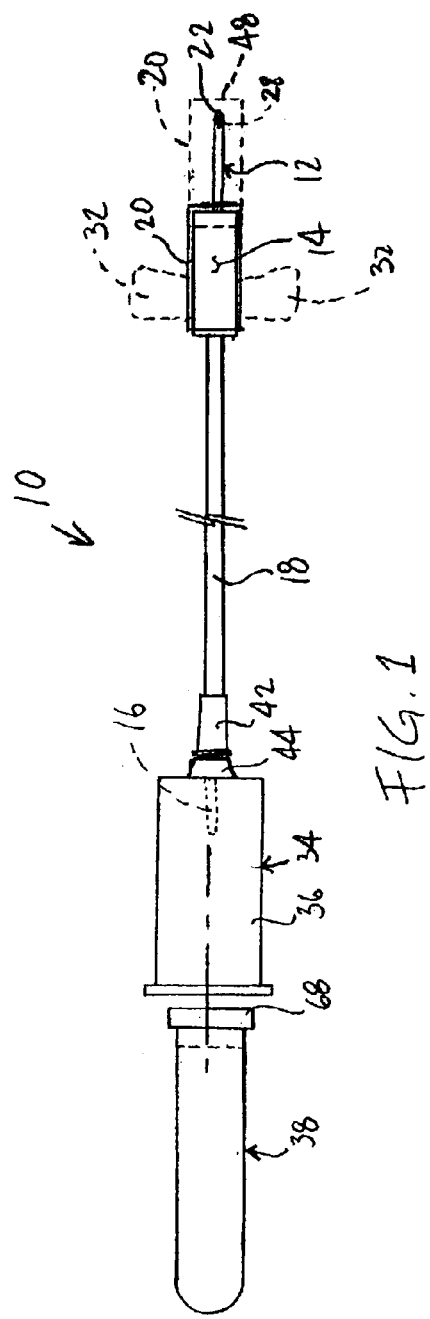
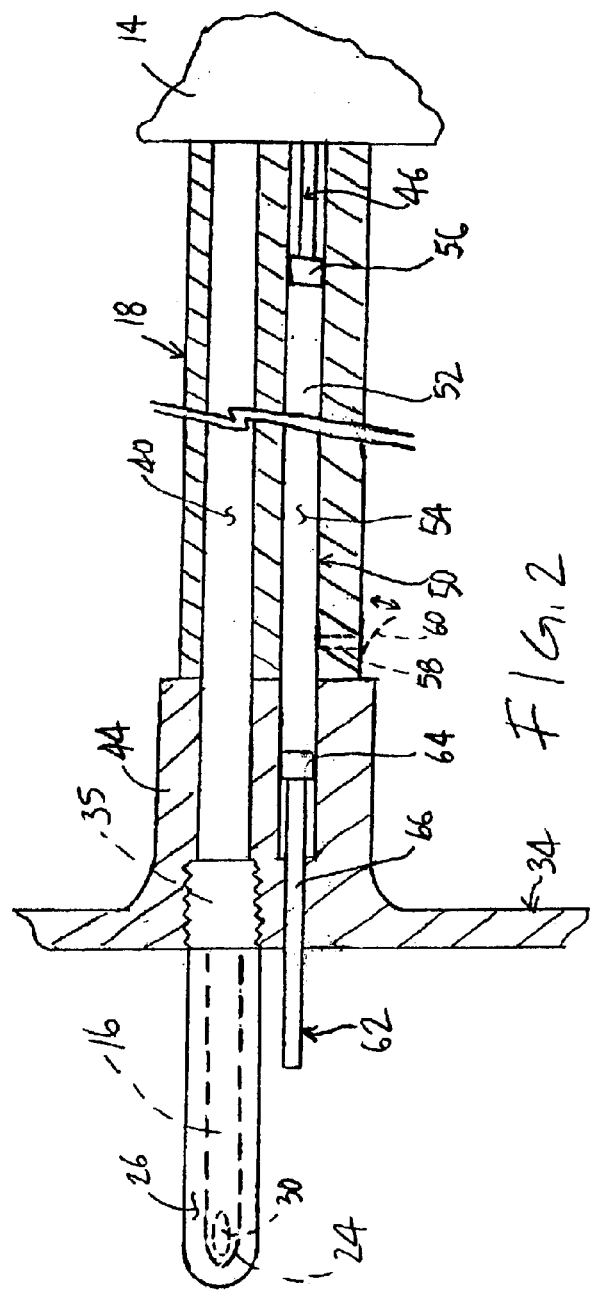

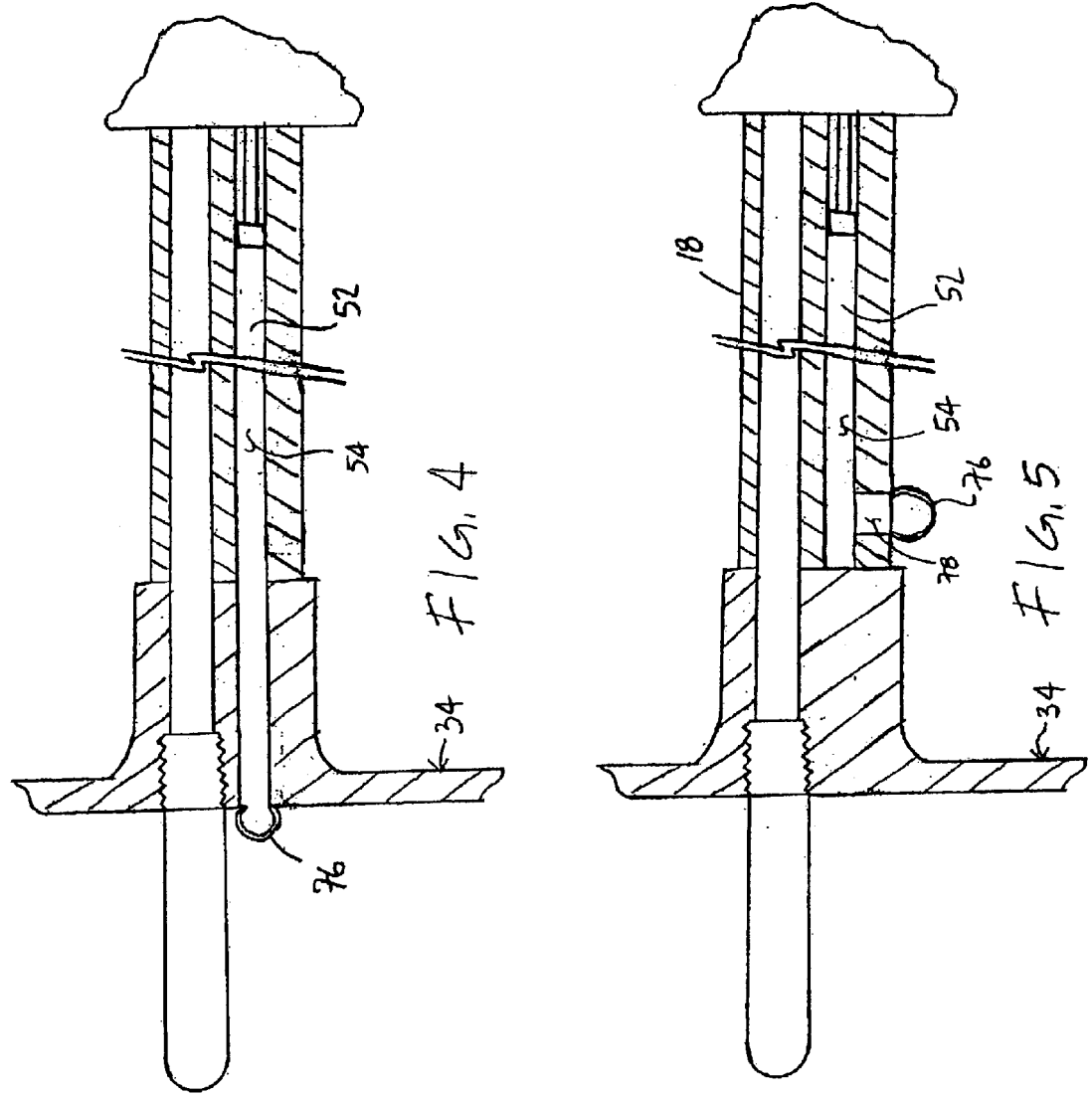

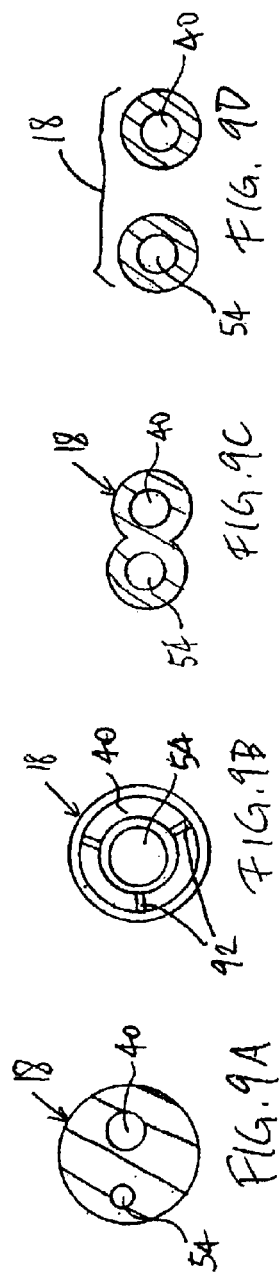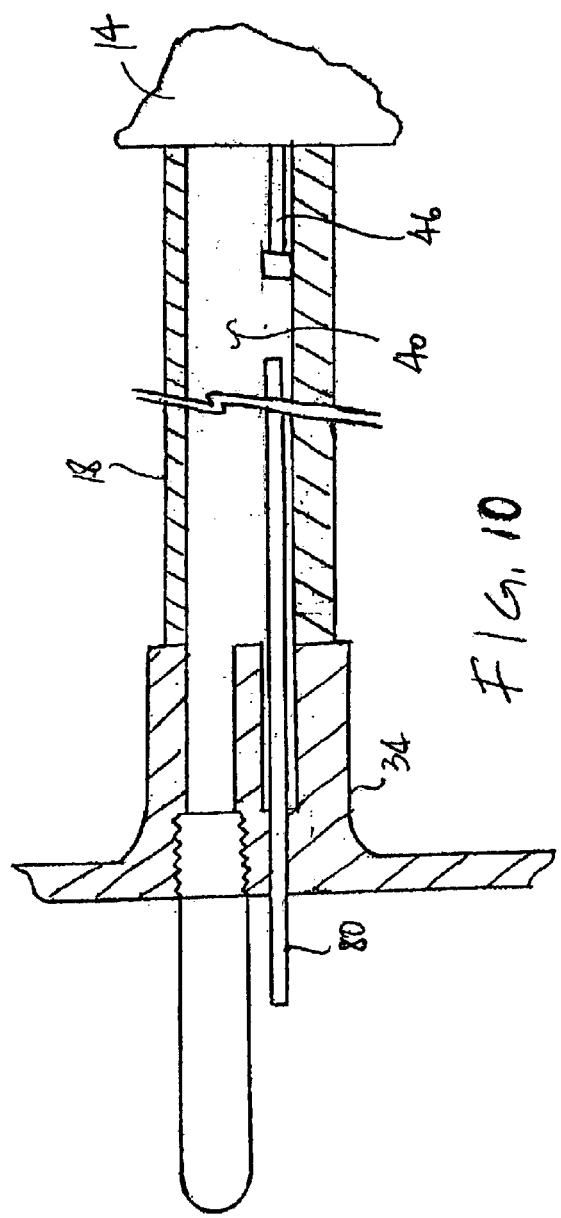

MEDICAL DEVICE WITH NEEDLE SAFETY SHIELDING

FIELD OF THE INVENTION

This invention relates to needle safety shielding for preventing inadvertent needle contact and, more particularly, to needle safety shielding for medical devices, such as blood collection sets, infusion sets, or fluid administration sets.

DESCRIPTION OF THE PRIOR ART

Blood collection sets are known in the prior art, wherein a needle cannula is provided for insertion into a patient's blood vessel with a flexible tube extending from the needle cannula to a second cannula, which is typically mounted onto a needle holder. The second cannula is used to pierce the septum of an evacuated blood collection tube or blood bag so that blood is transferred thereinto via the two cannulas and the connecting tube. The septum is typically a resealable pierceable elastomeric stopper.

As with most, if not all, sharp medical devices which are inserted into a patient (e.g., syringes; catheters; scalpels), inadvertent "sticks" by a needle cannula of a blood collection set into a practitioner post patient-insertion have become a major health concern, particularly with respect to the transmission of blood-borne diseases (e.g., AIDS). Various needle shielding and capping devices have been developed in the prior art to wholly, or at least partially, encapsulate used needle cannulas and prevent inadvertent contact therewith. Many of these devices require additional effort by a practitioner to be practiced, ranging from slipping a cap over the used needle cannula to actuating a mechanism that drives a shield about the needle cannula. In addition to these manually-activated safety devices, passive devices have been developed which cause shielding without any additional effort on behalf of a practitioner (i.e., the practitioner conducts a normal phlebotomy procedure without any additional steps with regard to shielding). For example, U.S. patent application Publication No. 2002/0099339 A1, published Jul. 25, 2002, to the assignee herein, discloses a needle cannula with a hub-mounted tip guard which drives forward upon being gripped and released during venipuncture by a practitioner.

SUMMARY OF THE INVENTION

With the present invention, needle safety shielding is provided for medical devices, such as blood collection sets. In a broadest sense, the invention is a medical device which includes a first needle cannula mounted to a first needle hub; a second needle cannula; tubing having at least a first lumen for establishing fluid communication between the first and second needle cannulas; an actuatable shield movable relatively to the first needle cannula upon actuation from an initial first position where the first needle cannula is at least partially exposed to a second position where a sharp distal end of the first needle cannula is at least partially encapsulated by the shield; and, an actuator for actuating the shield which is engageable at a location spaced from the first needle cannula and the first needle hub, preferably closer to the second needle cannula than to the first needle cannula or the first needle hub.

With the subject invention, both passive and manual actuation of a safety shield can be achieved. With passive actuation, no additional effort outside of normal operation of the medical device is necessary to cause needle shielding. If desired, manual actuation of the safety shield can be provided as an alternative, or in addition, to passive actuation. The invention can be used with various medical devices, but is particularly well-suited for intravenous infusion sets and blood collection sets. For illustrative purposes, discussion herein will relate to blood collection sets.

These and other features of the invention will be understood through a study of the following detailed description and accompanying drawings.

BRIEF DESCRIPTION OF THE DRAWINGS

FIG. 1 is a schematic of a blood collection set utilizing the subject invention;

FIG. 2 is an enlarged partial cross-sectional view of a first embodiment of the actuator including a fluid column;

FIG. 4 is a partial cross-sectional view showing an actuator including a bladder located to be engaged by a septum of a blood collection device;

FIG. 5 is a partial cross-sectional view showing a bladder formed on the tubing of the blood collection set;

FIGS. 9a–9d show various lumen and tube configurations; and,

FIG. 10 is a partial cross-sectional view showing the invention utilizing a single lumen.

DETAILED DESCRIPTION OF THE INVENTION

Figure 3B:
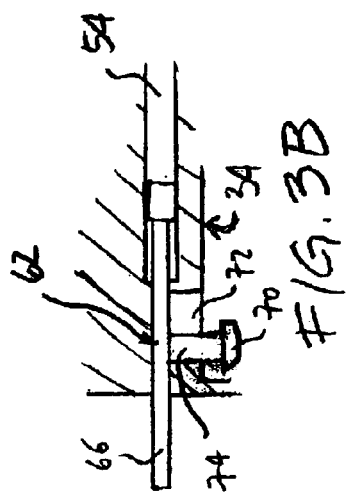
FIGS. 3a and 3b show piston structures having buttons mounted thereto, respectively.

With reference to FIG. 1, a medical device 10 is depicted (as shown therein, a blood collection set), which generally includes a first needle cannula 12 mounted to a first needle hub 14; a second needle cannula 16; and, tubing 18 for communicating the first and second needle cannulas 12 and 16. An actuatable shield 20 formed in accordance with any known design (such as axially shielding or pivotally shielding) is mounted to the first needle hub 14 so as to be movable from an initial position where a distal tip of the first needle cannula 12 is at least partially exposed to a second position where the shield is protecting or at least partially encapsulating the distal tip of the first needle cannula 12, as shown in dashed lines in FIG. 1.

The needle cannulas 12 and 16 are formed in any known fashion such as by drawn metal tubes or molded elastomers. The first needle cannula 12 includes a sharp distal end 22 for insertion into a patient. A proximal end 24 of the second needle cannula 16 may also be sharp to facilitate piercing of a septum of a blood collection device (e.g., evacuated blood collection tube; blood bag). The second needle cannula 16 may also be ensheathed in a compressible elastomeric sleeve 26. Both needle cannulas 12 and 16 are formed hollow and terminate respectively in openings 28, 30 which are positioned adjacent the ends 22, 24, respectively. With the second needle cannula 16 being inserted into an evacuated blood collection device, blood is drawn through the needle cannulas 12 and 16, via the openings 28 and 30, and into the blood collection device under the vacuum therein.

The first needle cannula 12 is mounted to the first needle hub 14 using any technique known to those skilled in the art.

As with conventional designs, wings 32 may be attached to the shield 20 and/or to the hub 14 so as to allow for securing the needle holder 14 to a patient.

A needle holder 34 may optionally be provided to which the second needle cannula 16 is mounted either directly, wherein the second needle cannula 16 is bonded to the needle holder 34, or indirectly, wherein the needle cannula 16b is bonded to a second needle hub 35 that is in turn secured to the needle holder 34 using any known technique such as a threaded connection or a snap-fit connection (luer fitting), as shown in FIG. 2. The needle holder 34 may be formed with a generally cylindrical body 36 formed to accommodate an evacuated blood collection tube 38. The needle holder 34 may take other forms; for example, to accommodate a blood bag (not shown).

The tubing 18, preferably low-gauge, flexible tubing, includes a first lumen 40 for communicating the first and second needle cannulas 12 and 16. The tubing 18 may be fixed relative to the first and second needle cannulas 12 and 16 using any technique known to those skilled in the art, whether directly by bonding or indirectly by an additional mating element such as a hub. By way of non-limiting example, the tubing 18 may be joined directly to a proximal end of the first needle cannula 12 (not shown) with such connection preferably being located within the first needle hub 14; and fixed to the needle holder 34 by a luer 42 mounted onto a hub 44 of the needle holder 34. The first lumen 40 may extend through a portion of the needle holder 34, such as through the hub 44, as shown in FIG. 2, to communicate with the second needle cannula 16.

The actuatable shield 20 may be of any design known to those skilled in the art which is trigger-activated to cause relative movement between the shield 20 and the first needle cannula 16 in urging the shield 20 into a position at least partially covering the first needle cannula 12: such relative movement may include the shield 20 sliding forward; the first needle cannula 12 being retracted into the shield 20; or, the shield 20 rotating relative to the first needle cannula 12 in a pivoting range of motion. Trigger-activated needle-shielding devices are known in the art. For example, a forward-sliding shield design is disclosed in copending U.S. application Ser. No. 10/165,407, to the assignee herein. The disclosure of U.S. application Ser. No. 10/165,407 is incorporated by reference herein. It is envisioned that the actuating mechanism for causing relative movement between the actuatable shield 20 and the first needle cannula 12 can be at least partially housed within the first needle hub 14. However, the specific design of the actuating mechanism to cause relative movement is not critical to the practicing of the invention. The invention does nevertheless require an actuation trigger. With reference to FIG. 2, a movable actuation trigger 46 is shown protruding from the needle hub 14. With the majority of actuating mechanisms, an elastic member (such as a spring) applies an urging force to cause relative movement to achieve needle shielding, the relative movement being inhibited by a locking member, such as a detent or a lug, until engagement of the actuation trigger 46. By causing movement of the actuation trigger 46, the first needle cannula 12 and/or the shield 20 are released to cause relative movement between the first needle cannula 12 and the shield 20. As will be readily recognized by those skilled in the art, any design or configuration can be used to translate the movement of the actuation trigger 46 into actuation of the shield 20.

The shield 20 may be of any configuration which allows for encapsulating at least a portion of the first needle cannula 12, particularly the sharp distal end 22. As shown in FIG. 1, with the actuation of the shield 20 involving linear movement, the shield 20 may have a tubular form which wholly encompasses the first needle cannula 12. As with conventional designs, distal end 48 of the shield may be left open. If so, the shield 20 should be formed with sufficient length to space the distal end 48 of the shield 20 from the distal end 22 of the first needle cannula 12. Other configurations which have limited structures surrounding the distal end 22 may be utilized, such as a cap, a band, and the like.

The actuatable shield 20 is actuated through the use of an actuator 50 which is engaged at a location spaced from the first needle cannula 12 and the first needle hub 14. Preferably, the actuator 50 is engageable at a location closer to the second needle cannula 16 than to the first needle cannula 12 or the first needle hub 14. With reference to FIGS. 2–6b, in a first embodiment, the actuator 50 includes a fluid column 52 disposed in a second lumen 54. The fluid column 52 can be defined by a liquid or a gas, and is preferably air. Various fluid (gas/liquid) components can be used in serial combination with sliding pistons interposed therebetween, if desired. The actuation trigger 46 is disposed in the second lumen, preferably having a piston head 56 in sealing engagement with the wall of the second lumen 54. Depending on the compressibility or incompressibility of the constituent material of the fluid column 52, a predetermined level of compression or displacement of the fluid column 52 will result in pressure being built up against the actuation trigger 46, resulting in movement thereof and actuation of the shield 20. The piston head 56 aids in development of the pressure build-up at the actuation trigger 46.

Since practitioners often kink the tubing 18 after insertion of the first needle cannula 12 into a patient and until it is established that an acceptable venipuncture has been made, it is preferred that a vent 58 be provided to communicate the second lumen 54 with atmosphere (as shown in dashed lines in FIG. 2). In this manner, pressure developed within the fluid column 52 upon kinking of the tubing 18 can be relieved upon venting through the vent 58 without inadvertently actuating the actuation trigger 46. As is readily appreciated, the vent 58 is for use with gas components of the fluid column 52, not liquid components. To prevent the ingress of dirt or contaminants into the vent 58, a valve 60, such as a flap valve, may be disposed over the vent 58 to have a normally-closed position.

To facilitate the compression or displacement of the fluid column 52, a piston 62 may be provided having a drive piston head 64 disposed in sealing engagement with the wall of the second lumen 54. The piston 62 also includes a stem 66.

Where passive engagement of the actuator 50 is desired, the piston 62 is disposed to have the stem 66 protrude from the needle holder 34 and preferably into the cylindrical body 36. The piston 62 is not fixed to the needle holder 34 so that sliding movement relative to the second lumen 54 can be achieved. Upon insertion of the second needle cannula 16 into a septum 68 of a blood collection device, such as the blood collection tube 38, the stem 66 is engaged by the septum 68 and, upon sufficient forward movement of the septum 68 into the needle holder 34, the piston 62 is caused to drive forward, resulting in compression or displacement of the fluid column 52, and actuation of the shield 20. The stem 66 must be formed with sufficient length to allow the piston 62 to travel sufficiently to compress or displace the fluid column 52 to cause actuation. It is also preferred that the drive piston head 64 be caused to traverse the vent 58 to seal off the vent 58 from the fluid column 52 in enhancing operation.

To achieve manual actuation, the needle holder 34 may be formed to resist forward movement of the septum 68 so that engagement of the stem 66 is not passive yet allows for proper positioning of the blood collection device for blood collection. For example, the needle holder 34 may include a flange or thread protruding inwardly from the cylindrical body 36 which is only by-passed by the septum 68 upon exertion or twisting of the blood collection device—additional effort and/or movement beyond normal insertion of the blood collection device into the needle holder 34. Thus, a threshold force of insertion of the septum 68 may be required to actuate the piston 62.

Figure 3A:
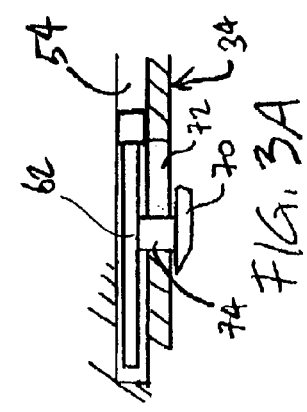

Alternatively, with reference to FIGS. 3a and 3b, if manual operation of the actuator 50 is desired, a button 70 may be provided which is fixed to the piston 62 through a slot 72 formed in the needle holder 34. The button 70 may be fixed in any manner such that movement of the button 70 results in movement of the piston 62. With this design, no portion of the piston 62 need to extend out of the second lumen 54. The button 70 may be formed to extend from the hub 44 or the cylindrical body 36, with a bridge 74 connecting the button 70 and the piston 62. Optionally, the bridge 74 can extend through a portion of the tubing 18.

As will be recognized by those skilled in the art, the configuration of the piston head 56, the piston 62 and the second lumen 54 may be formed in various configurations and shapes.

With the passive actuation described above, the shield 20 is caused to actuate upon insertion of the second needle cannula 16 into the septum 68 of an evacuated blood collection device. This actuation would thus occur with the first needle cannula 12 being inserted into a patient, wherein the shield 20 would bear against the skin of the patient and be prevented from covering the first needle cannula 12. Upon removal of the first needle cannula 12 from the patient, the shield 20 is free to fully actuate and cover the first needle cannula 12. With manual actuation, the shield 20 can be actuated at any time before, during, or after insertion of the first needle cannula 12. Depending upon the preference of the practitioner, an unobstructed view of the first needle cannula 12 inserted into the patient may be desired throughout the phlebotomy procedure and, thus, actuation may be desired towards the end of the procedure, or altogether after the procedure.

As a further variation, with reference to FIG. 3b, the button 70 may be provided with the piston 62, where the stem 66 also protrudes from the needle holder 34 and/or the tubing 18. With this structural arrangement, a redundant actuation system can be provided which allows for both passive and manual actuation. The ability to manually actuate this system, however, ends with passive actuation of the piston 62 with engagement of the septum 68, as described above.

Any device may be used to compress or displace the fluid column 52. For example, as shown in FIGS. 4 and 5, a compressible bladder 76 may be placed in fluid communication with the fluid column 52, such that upon compression of the bladder 76 the fluid column 52 may be compressed or displaced. Where passive actuation is desired, the bladder 76 may protrude from the needle holder 34 so as to be engaged by the septum 68 of a blood collection device. If manual actuation is desired, as shown in FIG. 5, the bladder 76 may protrude from the tubing 18 and/or the needle holder 34 to be engaged externally. Here, the bladder 76 is placed in communication with the second lumen 54 via a connecting channel 78. With the use of the bladder 76, it is preferred that no vent be provided, since no structure is provided to seal off a vent from the fluid column 52.

Figure 6B:
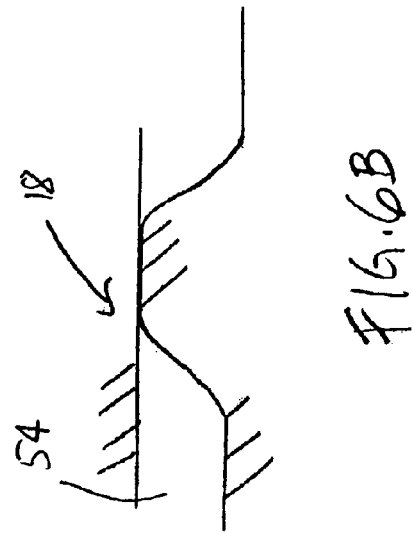
FIGS. 6a and 6b show different lumen configurations for enhancing control over actuation by the fluid column.
Figure 6A:
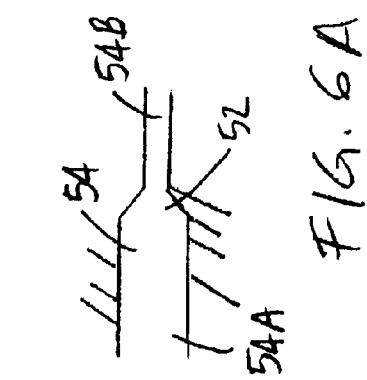

With the use of the fluid column 52, it is desired to obtain sufficient compression/displacement, if not excessive compression/displacement as a safety measure, to ensure proper operation. The second lumen 54 may be structurally configured to enhance control over compression/displacement. For example, as shown in FIG. 6a, the second lumen 54 can be formed with a larger cross-sectional area 54a which necks down to a smaller cross-sectional area 54b in which the actuation trigger 46 is disposed. In this manner, a larger force can be generated at the actuation trigger 46 upon compression/displacement in the fluid column 52. Other forms of manipulating the fluid column 52 may be employed. For example, to avoid inadvertent actuation of the shield 20 by impeding pressure build-up at the actuation trigger 46, the tubing 18 may be crimped to seal a portion or portions of the second lumen 54, as shown in FIG. 6b. To achieve actuation by the fluid column with one or more crimped portions, sufficient pressure build-up must be generated in the fluid column 52 which first un-crimps the tubing 18. As such, a threshold amount of work is required by the piston 62 or the bladder 76 prior to beginning work to compress/displace the fluid column 52.

Figure 7:
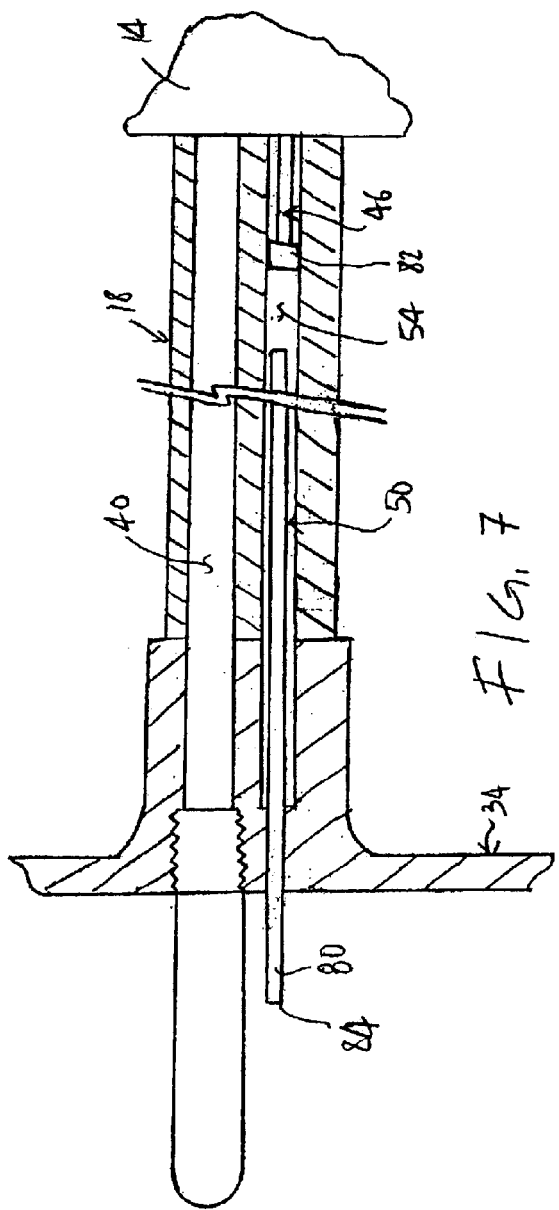
FIG. 7 is a partial cross-sectional view showing a second embodiment of the actuator including a movable rod.
Figure 8B:
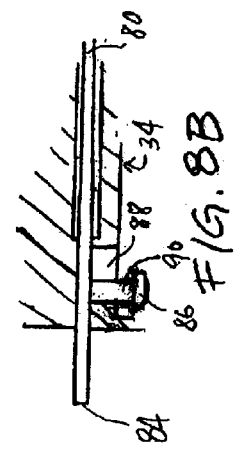
FIGS. 8a and 8b show rod structures having buttons mounted thereto, respectively.
Figure 8A:
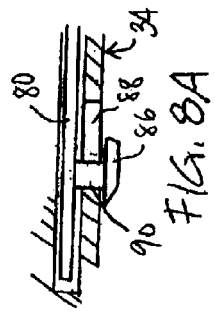

With reference to FIGS. 7–8b, a second embodiment of the actuator 50 is shown therein which includes a movable rod 80. In a preferred embodiment, the movable rod 80 is disposed in the second lumen 54, with sufficient length to engage and cause movement of the actuation trigger 46. A bumper 82 may be provided at the end of the actuation trigger 46 to facilitate force transfer to the actuation trigger 46 and/or to minimize misalignment between the rod 80 and the actuation trigger 46. The rod 80 is preferably formed of flexible material to bend with the tubing 18, such as from guide wire.

To obtain passive actuation using the rod 80, a proximal end 84 is formed to protrude from the needle holder 34 in the same manner as the stem 66 of the piston 62 described above. With engagement of the proximal end 84 by a septum of a blood collection device, the rod 80 is urged forwardly into engagement with the actuation trigger 46 to cause movement thereof, and actuation of the shield 20.

For manual actuation, the needle holder 34 may be formed to impede the insertion of the blood collection device, as described above with respect to the first embodiment. Alternatively, with reference to FIGS. 8a and 8b, a button 86 may be mounted to the rod 80 via a slot 88 formed through a portion of the needle holder 34. Movement of the button 86 will cause direct movement of the rod 80 in achieving actuation of the shield 20. The button 86 can be located externally of any portion of the needle holder 34 and/or the tubing 18 and connected to the rod 80 by a bridge 90. Where only manual actuation is desired, the rod 80 need not protrude from the needle holder 34. However, as shown in FIG. 8b, where a redundant configuration of passive and manual actuation is desired, the proximal end 84 may protrude to engage a septum as described above. As indicated above, the ability to manually actuate the shield is lost once passive actuation is engaged.

Although not shown, the rod 80 may be directly fixed to, or formed unitarily with, the actuation trigger 46, such that movement of the rod 80 results in direct movement of the actuation trigger 46. In addition, barbs may be appropriately disposed about the rod 80 to inhibit movement forwardly (e.g., to prevent inadvertent actuation) and/or rearwardly (e.g., to prevent unwanted rearward movement during actuation). The orientation and configuration of the barbs will correspond to the desired inhibition of motion.

The tubing 18 may take various configurations, as shown in FIGS. 9a–9d. With reference to FIGS. 9a and 9b, the tubing 18 may be a single tube which includes at least the first and second lumens 40 and 54, either in a side-by-side arrangement or in a concentric arrangement. If needed, webbing 92 may be provided to support the lumens 40 and 54 relative to each other. The concentric arrangement may require the actuator 50 to pass through a portion of the first lumen 40. For example, if the rod 80 is utilized as part of the actuator 50, the rod may need to be threaded through a portion of the first lumen 40 and into the second lumen 54. With reference to FIGS. 9c and 9d, two-tube configurations can be utilized, wherein two joined tubes (e.g., fused) may be used (FIG. 9c), as well as, two altogether separate tubes (FIG. 9d). The tubing 18 can be formed with various cross-sectional shapes and may include additional lumens for further purposes, such as testing or monitoring. In addition, the lumens 40 and 54 may be formed of various cross-sectional shapes.

As will be appreciated by those skilled in the art, the actuator 50 may take various forms to operate in accordance with the principles described herein. It is desired to provide an actuator which enables actuation of the shield 20 from a position spaced from the first needle cannula 12 and the first needle hub 14, and, preferably, from a position that is closer to the second needle cannula 16. In addition, the second lumen 54 need not be utilized or provided. For example, as shown in FIG. 10, the rod 80 may be disposed to extend through the first lumen 40. Alternatively, although not shown, the rod 80 may be located externally of the tubing 18, such as being coiled thereabout to engage the actuation trigger 46. As a further variation, the actuation trigger 46 can also be located externally of the tubing 18.

While the invention has been described in relation to the preferred embodiments with several examples, it will be understood by those skilled in the art that various changes may be made without deviating from the spirit and scope of the invention as defined in the appended claims.

What is claimed is:

1. A medical device comprising:
    a first needle cannula having proximal and distal ends, at least said distal end being sharp for insertion into a patient;
    a first needle hub, said first needle cannula being mounted to said first needle hub;
    a second needle cannula;
    tubing having at least a first lumen for establishing fluid communication between said first needle cannula and said second needle cannula;
    an actuatable shield for selectively at least partially encapsulating said distal end of said first needle cannula, said shield being movable relatively to said first needle cannula upon actuation from an initial first position wherein said first needle cannula is at least partially exposed to a second position wherein at least said distal end of said first needle cannula is at least partially encapsulated by said shield;
    an actuator for actuating said shield, said actuator being engageable at a location spaced from said first needle cannula and said first needle hub to cause actuation of said shield; and,
    a second lumen in communication with an actuation trigger of said shield, said actuator being at least partially disposed in said second lumen, wherein said actuator includes a fluid column disposed in said second lumen, wherein, compression or displacement of a fluid in said fluid column causes exertion of pressure by said fluid against said actuator trigger, wherein upon reaching a predetermined level of said compression or said displacement, said pressure exerted by said fluid against said actuation trigger activates said trigger, thereby actuating said shield.

2. A device as in claim 1, wherein said second lumen includes a vent to atmosphere.

3. A device as in claim 2, wherein a valve regulates flow from said second lumen and through said vent.

4. A device as in claim 1, wherein said actuator includes a piston disposed in said second lumen, said piston being slidable to cause said predetermined level of compression or displacement of said fluid column to actuate said shield.

5. A device as in claim 4, wherein a proximal end of said piston is located to engage a septum in which said second needle cannula is inserted, said engagement causing sliding movement of said piston and actuating said shield.

6. A device as in claim 4, wherein said actuator includes a button fixed to said piston, movement of said button causing movement of said piston.

7. A device as in claim 1, wherein said actuator includes a bladder in communication with said fluid column, compression of said bladder causing said predetermined level of compression or displacement of said fluid column to actuate said shield.

8. A device as in claim 7, wherein said bladder is located to engage a septum into which said second needle cannula is inserted, said engagement causing compression of said bladder and actuating said shield.

9. A device as in claim 1, wherein said second lumen is formed in said tubing.

10. A device as in claim 1, wherein said tubing includes at least first and second tubes, said first lumen being formed in said first tube, said second lumen being formed in said second tube.

11. A device as in claim 1 further comprising a needle holder, said second needle cannula being mounted to said needle holder.

12. A device as in claim 1, wherein said actuator being engageable at a location closer to said second needle cannula than said first needle cannula.

13. A medical device comprising:
    a first needle cannula having proximal and distal ends, at least said distal end being sharp for insertion into a patient;
    a first needle hub, said first needle cannula being mounted to said first needle hub;
    a second needle cannula;
    a first lumen for establishing fluid communication between said first needle cannula and said second needle cannula; an actuatable shield for selectively at least partially encapsulating said distal end of said first needle cannula, said shield being movable relatively to said first needle cannula upon actuation from an initial first position wherein said first needle cannula is at least partially exposed to a second position wherein at least said distal end of said first needle cannula is at least partially encapsulated by said shield; and,
    a second lumen containing a fluid column, said second lumen being in communication with an actuation trigger of said shield, wherein, compression or displacement of a fluid in said fluid column causes exertion of pressure by said fluid against said trigger, wherein upon reaching a predetermined level of said compression or said displacement, said pressure exerted by said fluid against said actuation trigger activates said trigger, thereby actuating said shield.

14. A device as in claim 13, wherein said second lumen includes a vent to atmosphere.

15. A device as in claim 14, wherein a valve regulates flow from said second lumen and through said vent.

16. A device as in claim 13 further comprising a piston disposed in said second lumen, said piston being slidable to cause said predetermined level of compression or displacement of said fluid column to actuate said shield.

17. A device as in claim 16, wherein a proximal end of said piston is located to engage a septum in which said second needle cannula is inserted, said engagement causing sliding movement of said piston and actuating said shield.

18. A device as in claim 16, wherein said actuator includes a button fixed to said piston, movement of said button causing movement of said piston.

19. A device as in claim 13, further comprising a bladder in communication with said fluid column, said bladder being compressible to cause said predetermined level of compression or displacement of said fluid column to actuate said shield.

20. A device as in claim 19, wherein said bladder is located to engage a septum into which said second needle cannula is inserted, said engagement causing compression of said bladder and actuating said shield.

21. A device as in claim 13, wherein said first and second lumens are formed in a common tubing.

22. A device as in claim 13, wherein said first and second lumens are formed in separate tubes.

23. A device as in claim 13, further comprising a needle holder, said second needle cannula being mounted to said needle holder.

* * * * *